(12) United States Patent
Conzelmann et al.

(10) Patent No.: US 7,259,132 B2
(45) Date of Patent: Aug. 21, 2007

(54) SHAVING AID

(75) Inventors: Stefanie Conzelmann, Hamburg (DE); Peter Maurer, Neumünster (DE); Ilka Oelrichs, Tornesh (DE)

(73) Assignee: Beiersdorf AG, Hamburg (DE)

( * ) Notice: Subject to any disclaimer, the term of this patent is extended or adjusted under 35 U.S.C. 154(b) by 135 days.

(21) Appl. No.: 11/248,750

(22) Filed: Oct. 12, 2005

(65) Prior Publication Data

US 2006/0111262 A1  May 25, 2006

(30) Foreign Application Priority Data

Oct. 12, 2004  (DE) .................. 10 2004 049 773

(51) Int. Cl.
*A61Q 9/02* (2006.01)
*A61K 8/36* (2006.01)
*A61K 8/41* (2006.01)
*A61K 8/45* (2006.01)
*C11D 9/22* (2006.01)

(52) U.S. Cl. ................. 510/120; 510/121; 510/129; 510/140; 510/151; 510/155; 510/406; 510/421; 510/437; 510/473; 510/481; 510/499; 424/43; 424/45; 424/73

(58) Field of Classification Search ........... 510/120, 510/121, 129, 140, 151, 155, 406, 421, 437, 510/473, 481, 499; 424/43, 45, 73
See application file for complete search history.

(56) References Cited

U.S. PATENT DOCUMENTS

| 3,923,970 A | 3/1974 | Brewer |
| 5,279,819 A * | 1/1994 | Hayes .................. 424/73 |
| 5,500,211 A | 3/1996 | George et al. |
| 5,858,343 A | 1/1999 | Szymczak |
| 6,352,689 B1 | 3/2002 | Szymczak |
| 2002/0182234 A1 | 12/2002 | Reidel et al. |
| 2003/0021760 A1 | 1/2003 | Kumar et al. |
| 2004/0258628 A1 | 12/2004 | Riedel et al. |
| 2005/0074471 A1 | 4/2005 | Bleckmann et al. |

FOREIGN PATENT DOCUMENTS

| DE | 100 63 342 A1 | 6/2002 |
| DE | 102 39 712 A1 | 3/2004 |
| EP | 05 03 004 B1 | 5/1996 |
| FR | 27 89 397 A1 | 8/2000 |
| WO | 91/07943 | 6/1991 |
| WO | 92/16188 | 10/1992 |
| WO | 02/074256 | 9/2002 |
| WO | 03/041663 | 5/2003 |

OTHER PUBLICATIONS

German Search Report for corresponding German Application No. 10 2004 049 773.7 dated Mar. 14, 2005.

* cited by examiner

*Primary Examiner*—Brian Mruk
(74) *Attorney, Agent, or Firm*—Greenblum & Bernstein, P.L.C.

(57) ABSTRACT

The invention is a preparation comprising an oil-in-water emulsion containing soap, the emulsion further comprising: (a) 4-12% by weight of at least one fatty acid with 12 to 18 carbon atoms, (b) 3-8% by weight of at least one trialkanolamine, (c) 1-8% by weight of at least one nonionic emulsifier, (d) 0-3% by weight of a fatty alcohol or fatty alcohol mixture, (e) 0.1-6% by weight of one or more emollients, (f) 1-10% by weight propellant with a vapor pressure of 76 to 420 kPa at 20° C., (g) 0-1% by weight of at least one cellulose derivative, and (h) 0.1-4% by weight of at lest one glycerol polyglycol ether isostearate, wherein the oil-in-water emulsion is free from fatty acid diethanolamides, and wherein the preparation is suitable for filling in an aerosol container. The invention also includes a pressurized gas container containing the preparation.

18 Claims, No Drawings

SHAVING AID

FIELD OF THE INVENTION

The present invention concerns shaving aids. A distinction is made between shaving creams and shaving gels. Shaving foams are formulated in such a way that the preparation containing an aerosol can be removed from the container in the form of foam. Quality shaving foams are distinguished by a fine-porous, abundant and stable foam.

BACKGROUND OF THE INVENTION

Shaving gels, on the other hand, are formulated in such a way that the preparation also containing an aerosol can be removed from the container in non-foamed form, whereby it later foams on the skin or in the hand through vaporization of the propellant contained in the preparation in response to body heat.

In both cases, the skill of the formulation consists of attaining a good compromise in respect to foam texture, gel consistency, stability and visual appearance through a suitable choice of thickening agents and foam stabilizers.

A frequent ingredient of such preparations is cocamide DEA. This compound belongs to the group of fatty acid diethanolamides. It is a reaction product from diethanolamine (DEA), from the family of alkanolamines and free fatty acids, obtained from coconut oil. Free DEA, which only occurs in significant amounts in poor qualities, is able to form nitrosamines in combination with N-nitrosating substances, such as nitrites. As these nitrosamines exhibit a carcinogenic potential, it is therefore advisable to avoid their formation. This can easily be achieved through correct use of the raw material. Unfortunately, chemical correlations are often depicted inaccurately or even incorrectly in publications, e.g. in consumer magazines. As a result, although fatty acid diethanolamides can indeed be used in brand products, the desire to avoid their use has meanwhile become prevalent.

In surfactant preparations, fatty acid diethanolamides exhibit the additional benefit of acting as a so-called "foam booster": at the same time, the stability, formation and structure of the foam is significantly improved, in other words several requirements are fulfilled by an ingredient at the same time. Consequently, there is no alternative to cocamide DEA in shaving preparations, as the unique combination of all properties is not attained.

It would be desirable to find an ingredient with similar effects, which does not manifest the problem described above. As this problem has been known for quite some time, many substitutes for fatty acid diethanolamides have already been revealed. Despite the wide range offered, no suitable substitute could so far be found, which can advantageously be used in shaving preparations and which fulfills all the above requirements at the same time in a comparable quality.

International patent application WO 96/09032 discloses soap-free shaving preparations based on sarcosinates with a pH value in the region pH 5-7. In contrast to this, preparations corresponding to the invention contain soap and exhibit a pH value >7.

Patent specification U.S. Pat. No. 3,923,970 discloses shaving preparations which, amongst other ingredients, contain polyoxyethylene oleyl ethers with an HLB in the range 1-9 or lauramide DEA. In contrast to this, preparations corresponding to the invention are free of these.

Patent specification EP 503004 discloses shaving preparations which, amongst other ingredients, contain polysiloxane/polyether copolymers. In contrast to this, preparations corresponding to the invention are free of these.

The international patent application WO 98/33473 discloses shaving preparations which, amongst other ingredients, contain polyethoxylated polyvinylpyrrolidones. In contrast to this, preparations corresponding to the invention are free of these.

European patent application 576615 discloses self-foaming O/W shaving creams containing water, soap components, surfactant, propellant, emollients and foam stabilizers from the group of fatty alkanolamides, e.g. lauramide DEA. Nevertheless, no information is disclosed concerning preparations with an additional content of cellulose derivatives while free of fatty acid alkanolamides at the same time.

SUMMARY OF THE INVENTION

On this basis of this, the task of the present invention involved finding a thickening agent surfactant combination which does not favor the formation of nitrosamines during manufacture and at the same time, enables an improved gliding of the razor blade over the skin.

It was revealed to the expert in an unforeseeable manner that oil-in-water emulsions containing soap, which are free from fatty acid diethanolamides and which are suitable for filling in aerosol containers, comprising (a) 4 to 12% by weight fatty acids with 12 to 18 carbon atoms, (b) 3 to 8% by weight trialkanolamines as well as further components, (c) 1 to 8% by weight, preferably 2 to 6% by weight of a nonionic emulsifier, (d) 0 to 3% by weight of a fatty alcohol or fatty alcohol mixture, (e) 0.1 to 6% by weight, particularly preferred 0.5 to 5% by weight of one or more emollients, (f) 1 to 10, particularly preferred 2 to 5% by weight propellant with a vapor pressure of 76 to 420 kPa at 20° C., (g) 0 to 1% by weight, preferably 0.1 to 1% by weight of a cellulose derivative, and (h) 0.1 to 4, particularly preferred up to 3, especially preferred up to 2% by weight glycerol polyglycol ether isostearates, particularly preferred those such with 70 to 110 ethylene oxide units, in relation to the total weight of the preparation respectively, exhibit properties which remedy the shortcomings of the prior art.

These combinations have a simultaneous thickening and lubricating effect, with the result that the razor blade can glide over the skin better. To this end, glycerol polyglycol ether isostearates act as gel forming agents and thickeners, trialkanolamines promote foam formation and provide help in setting the foam structure, while nonionic emulsifiers play a role in the formation of a gliding film on the skin. Preparations of such type can be single or multiple phase, two-phase types being preferred.

DETAILED DESCRIPTION OF THE PREFERRED EMBODIMENTS

It was also discovered as preferable if the nonionic emulsifier or emulsifiers exhibit an HLB value of at least 14. At the same time, it is preferable if the emulsifier or emulsifiers are selected from the group of fatty acid alkoxylates with 10 to 40, particularly preferred 15 to 30 alkoxy units. It is further preferable if the cellulose derivative or derivatives are selected from the group hydroxypropylmethylcellulose, hydroxyethylcellulose, and hydroxypropylcellulose. It is also preferable if glycerol polyglycolether-90-isostearate is used as a glycerol polyglycolether isostearate. Preparations corresponding to the invention are preferably extant in the form of foams extractable from a pressurized gas container or alternatively as shaving gels extractable from a pressurized gas container. Such gels can be transparent, diaphanous or opaque. It is particularly preferred if the pressurized gas container exhibits two chambers. The invention also comprises vessels containing the preparations corresponding to the invention.

It is advantageous if the oil content in gels is 0 to 2% by weight, particularly preferred 0.5 to 1.5% by weight. It is also advantageous if the oil content in foams is 0 to 6% by weight, particularly preferred 0.25 to 1% by weight.

The omission of one of the individual components influences the unique properties of the total composition. All the components cited of the preparations corresponding to the invention are therefore absolutely essential in order to realize the invention.

Preparations corresponding to the invention can also advantageously contain further surfactants, antioxidants, vitamins, preservatives and water-soluble dyes.

Surfactants

Surfactants are amphiphilic substances which can dissolve organic, non-polar substances in water. As a result of their specific molecule degradation with at least one hydrophilic and one hydrophobic molecular part, they enable a reduction in the surface tension of the water, wetting of the skin, facilitation of dirt removal and dissolving, easy rinsing and—depending on requirements—foam regulation.

The hydrophilic parts of a surfactant molecule usually involve polar functional groups, for example $-COO^-$, $-OSO_3^{2-}$, $-SO_3^-$, while the hydrophobic parts mostly represent non-polar hydrocarbon residues. Surfactants are generally classified according to the type and charge of the hydrophilic molecular part. Four groups can be distinguished for this:

Anionic surfactants,
Cationic surfactants,
Amphoteric surfactants and
Nonionic surfactants.

Anionic surfactants generally exhibit carboxylate, sulfate or sulfonate groups as functional groups. In aqueous solution, they form negatively charged organic ions in an acidic or neutral environment. Cationic surfactants are almost exclusively characterized by the presence of a quaternary ammonium group. In aqueous solution, they form positively charged organic ions in an acidic or neutral environment. Amphoteric surfactants contain both anionic and cationic groups and consequently behave like anionic or cationic surfactants in aqueous solution, depending on the pH value.

In a highly acidic environment they have a positive charge and in an alkaline environment they exhibit a negative charge. In a neutral pH range, however, they are zwitterionic, as the following example is intended to reveal:

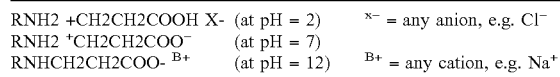

| | | |
|---|---|---|
| $RNH_2 + CH_2CH_2COOH$ $X^-$ | (at pH = 2) | $X^-$ = any anion, e.g. $Cl^-$ |
| $RNH_2$ $^+CH_2CH_2COO^-$ | (at pH = 7) | |
| $RNHCH_2CH_2COO^-$ $B^+$ | (at pH = 12) | $B^+$ = any cation, e.g. $Na^+$ |

Typical of nonionic surfactants are polyether chains. Nonionic surfactants do not form ions in an aqueous medium.

A. Anionic Surfactants

Anionic surfactants Which may be used advantageously include:

Acylamino acids (and their salts), such as
1. Acyl glutamates, for example sodium acyl glutamate, Di-TEA-palmitoyl aspartate, and sodium caprylic/capric glutamate,
2. Acyl peptides, for example palmitoyl-hydrolyzed milk protein, sodium cocoyl-hydrolyzed soya protein and sodium/potassium cocoyl-hydrolyzed collagen,
3. Sarcosinates, for example myristoyl sarcosin, TEA-lauroyl sarcosinate, sodium lauroyl sarcosinate and sodium cocoyl sarcosinate,
4. Taurates, for example sodium lauroyl taurate and sodium methylcocoyl taurate,
5. Acyl lactylates, lauroyl lactylate, caproyl lactylate,
6. Alaninates;

Carboxylic acids and derivatives, such as
1. Carboxylic acids, for example, lauric acid, aluminum stearate, magnesium alkanolate, and zinc undecylenate,
2. Ester carboxylic acids, for example, calcium stearoyl lactylate, laureth-6 citrate, and sodium PEG-4 lauramide carboxylate,
3. Ether carboxylic acids, for example, sodium laureth-13 carboxylate, and sodium PEG-6 cocoamide carboxylate;

Esters of phosphoric acid and salts, such as for example dilaureth-4 phosphate;

Sulfonic acids and salts, such as
1. Acyl isethionate, for example, sodium-ammoniumcocoyl isethionate,
2. Alkylaryl sulfonates,
3. Alkyl sulfonates, for example sodium coco monoglyceride sulfate, sodium $C_{12-14}$ olefin-sulfonate, sodium lauryl sulfoacetate and magnesium PEG-3 cocamide sulfate,
4. Sulfosuccinates, for example dioctyl sodium sulfosuccinate, disodium laureth sulfosuccinate, disodium lauryl sulfosuccinate, disodium undecylenamido-MEA-sulfosuccinate, and PEG-5 lauryl citrate sulfosuccinate;

Esters of sulfuric acid, such as:
1. Alkyl ether sulfate, for example sodium, ammonium, magnesium, MIPA, TIPA, laureth sulfate, sodium myreth sulfate and sodium $C_{12-13}$ pareth sulfate,
2. Alkyl sulfates, for example sodium, ammonium and TEA lauryl sulfate.

B. Cationic Surfactants

Cationic surfactants Which may be used advantageously include
1. Alkylamines,
2. Alkylimidazoles,
3. Ethoxylated amines,
4. Quaternary surfactants, and
5. Esterquats.

Quaternary surfactants contain at least one nitrogen atom, which is covalently bonded to 4 alkyl or aryl groups. Irrespective of the pH value, this results in a positive charge. Advantageous quaternary surfactants are alkylbetaine, alkylamidopropylbetaine, and alkylamidopropyl-hydroxysulfaine. The cationic surfactants that may be used in accordance with the invention can also be selected from quaternary ammonium compounds, in particular benzyltrialkyl ammoniumchlorides or bromides, such as for example, benzyldimethylstearyl ammonium chloride, furthermore alkyltrialkyl ammonium salts, for example, cetyltrimethyl ammonium chloride or bromide, alkyldimethylhydroxyethyl ammonium chloride or bromide, dialkyldimethyl ammonium chloride or bromide, alkylamide ethyltrimethylammonium ether sulfates, alkylpyridinium salts, for example, lauryl or cetyl pyrimidinium chloride, imidazoline derivatives and compounds having cationic character, such as amine oxides, for example, alkyldimethylamine oxides or alkylaminoethyl dimethylamine oxides. The use of cetyltrimethyl ammonium salts is particularly advantageous.

C. Amphoteric Surfactants

Amphoteric surfactants which may advantageously be used include
1. Acyl-/dialkyl ethylenediamine, for example, sodium acyl amphoacetate, disodiumacyl amphodipropionate, disodium alkyl amphodiacetate, sodium acylamphohydroxypropyl sulfonate, disodium acyl amphodiacetate, and sodium acyl amphopropionate.
2. N-alkylamino acids, for example, aminopropyl alkylglutamide, alkylaminopropionic acid, sodium alkylimidodipropionate and lauroamphocarboxyglycinate.

D. Nonionic Surfactants

Nonionic surfactants which may advantageously be used include:
1. Alcohols,
2. Aminoxides, such as cocoamidopropylamine oxide,
3. Esters, which result from the esterification of carboxylic acids with ethylene oxide, glycerin, sorbitan, or other alcohols,
4. Ethers, for example, ethoxylated/propoxylated alcohols, ethoxylated/propoxylated esters, ethoxylated/propoxylated glycerol esters, ethoxylated/propoxylated cholesterols, ethoxylated/propoxylated triglyceride esters,
5. Ethoxylated/-propoxylated lanolin, ethoxylated/propoxylated polysiloxanes, propoxylated POE-ethers, and alkyl polyglycosides, such as lauryl glucoside, decyl glycoside and coco glycoside;
6. Sucrose esters, sucrose ethers;
7. Polyglycerol esters, diglycerol esters, monoglycerol esters;
8. Methylglucose esters, esters of hydroxy acids It may also be advantageous to use a combination of anionic and/or amphoteric surfactants with one or more nonionic surfactants.

Antioxidants

The generally familiar antioxidants can be used. Particularly preferred, however, are tocopherols and derivatives (e.g. vitamin E acetate) as well as butylhydroxytoluene and butylhydroxyanisol.

Vitamins

The generally familiar vitamins can be used, also in the form of derivatives and/or salts thereof.

Preservatives

The preparations corresponding to the invention can advantageously contain according to the invention one or more preservatives. Advantageous preservatives in the sense of the present invention are, for example, parabens (i.e. p-hydroxybenzoic acid alkyl esters, such as methyl-, ethyl-, propyl- and/or butyl paraben), phenoxyethanol, ethanol, benzoic acid and other similar preservatives.

Advantageous according to the invention are one or more preservatives in a concentration of 0.001 to 2% by weight, preferably 0.01 to 1.5% by weight and particularly preferred 0.05 to 1% by weight, in relation to the total weight of the preparation respectively. Here the weight data refers to the composition of the preparation before drying.

Dyes and Pigments

It might also be advantageous in the sense of the present invention to incorporate dyes and/or pigments in the preparations corresponding to the invention.

The dyes and pigments can be selected from the corresponding positive list of the Cosmetics Ordinance or the EC list of cosmetic dyes. In most cases, they are identical to the dyes permissible for food. Advantageous color pigments can typically be seen in the following list: The Color Index Numbers (CIN) are taken from the *Rowe Colour Index, 3$^{rd}$ Edition, Society of Dyers and Colourists, Bradford, England,* 1971.

| Chemical or other designation | CIN | Color |
| --- | --- | --- |
| 4-[(-4-N-ethyl-p-sulfobenzylamino)-phenyl-(4-hydroxy-2-sulfo-phenyl)-(methylene)-1-(N-ethylN-p-sulfobenzyl)-2,5 cyclohexadienimine] | 42053 | green |
| (N-ethyl-p-sulfobenzyl-amino)-phenyl-(2-sulfophenyl)-methylene-(N-ethyl-N-p-sulfo-benzyl)$\Delta^{2,5}$-cyclohexadienimine | 42090 | blue |
| Quninophthalone disulfonic acid | 47005 | yellow |

Water soluble dyes can preferably be used.

With all of these, it is possible in individual cases that the above concentration data can be exceeded or fallen short of slightly, preparations corresponding to the invention nevertheless being obtained. This should not come as unexpected to the expert in view of the wide diversity of suitable components for such preparations, with the result that the basis of the present invention is not lost in the event of such excesses or shortfalls.

The following examples are intended to clarify the present invention without restricting it. The numerical values in the examples signify weight percentages, in relation to the total weight of the respective preparations.

EXAMPLES

Examples for Later-Foaming Shaving Gels

| Product designation | Amount/% | Amount/% | Amount/% | Amount/% |
| --- | --- | --- | --- | --- |
| Palmitic acid | 8.90 | 7.00 | 9.30 | 4.00 |
| Stearic acid | | 1.00 | | 4.00 |
| Triethanolamine | 7.00 | 5.5 | 7.15 | 6.5 |

-continued

| Product designation | Amount/% | Amount/% | Amount/% | Amount/% |
|---|---|---|---|---|
| Polyethylene glykol(20)oleyl ether | 6.30 | 4.00 | 5.50 | 7.00 |
| Na-lauryl myristyl ether sulfate | | | 3.00 | 2.50 |
| Fatty acid amido alkyl betaine | | 2.00 | | 1.50 |
| Sorbitol | 4.20 | | 3.50 | |
| Glycerin | | 4.00 | | 5.00 |
| Propylene Glycol | | | 3.50 | |
| Cocodiethanolamide | 1.05 | | | |
| Glycerol polyglycol (90) ether isostearate/Polyethylene glycol (2) lauryl ether[1] | | 0.50 | 1.00 | |
| Paraffin oil | 1.05 | 1.00 | 1.50 | |
| Polyisobutylene | 0.53 | 0.30 | 1.00 | 0.85 |
| Hydroxyethylcellulose | 0.53 | 0.50 | 0.50 | 0.50 |
| PEG-14 M | 0.11 | 0.30 | 0.15 | |
| Isopentane | 3.95 | 3.95 | 3.95 | 3.95 |
| Isobutane | 1.30 | 1.30 | 1.30 | 1.30 |
| Propylparaben | 0.09 | q.s. | q.s | q.s. |
| Methylparaben | 0.13 | q.s. | q.s | q.s. |
| Butylhydroxytoluene | 0.03 | 0.03 | 0.03 | 0.03 |
| Dye | q.s. | q.s. | q.s | q.s. |
| Perfume | q.s. | q.s. | q.s | q.s. |
| Water | add.100 | add.100 | add.100 | add.100 |
| Total: | 100.00 | 100.00 | 100.00 | 100.00 |

[1]Glycerol isostearate polyglycol ether/Fatty alcohol polyglycol ether 77% available under the trade name OXETAI VD 92 from the company Zschimmerer & Schwarz.

Examples for Shaving Foams

| Product designation | Amount [%] | Amount [%] | Amount [%] | Amount [%] |
|---|---|---|---|---|
| Palmitic acid | | 2.75 | 5.00 | 2.00 |
| Stearic acid | 5.90 | 2.75 | | 4.00 |
| Glycerol | 3.75 | 2.00 | 5.00 | 4.00 |
| Na-lauryl myristyl ether sulfate (25%) | 3.60 | 5.00 | | 1.80 |
| Fatty acid amido alkyl betaine | | 1.50 | 2.70 | 1.90 |
| Triethanolamine | 3.50 | 3.80 | 3.10 | 4.15 |
| Ethylene glycol monolauryl ether [polyethylene glycol (23) laury lether] | 2.95 | 2.75 | 5.00 | 4.00 |
| Coco-caprylates/caprates | | | | 0.50 |
| Glycerol polyglycol (90) ether Isostearate/Polyethylene glycol (2) lauryl ether[1] | | 0.10 | 0.5 | |
| Paraffin oil | | 1.00 | | |
| Hydroxypropylmethylcellulose | | | 0.15 | |
| Dimethylsiloxane glycol copolymer | | 0.50 | 0.20 | |
| Stearyl alcohol | | 0.10 | | 0.50 |
| Propylparaben | q.s. | q.s. | q.s. | q.s. |
| Isobutane | 2.90 | 2.90 | 2.90 | 2.90 |
| Propane | 0.95 | 0.95 | 0.95 | 0.95 |
| Butane | 0.20 | 0.20 | 0.20 | 0.20 |
| Methylparaben | q.s. | q.s. | q.s. | q.s. |
| Perfume | q.s. | q.s. | q.s. | q.s. |
| Aqua | add.100 | add.100 | add.100 | add.100 |
| Total: | 100.00 | 100.00 | 100.00 | 100.00 |

That which is claimed:
1. A preparation comprising an oil-in-water emulsion comprising soap, the emulsion further comprising:
   (a) 4 to 12% by weight of at least one fatty acid with 12 to 18 carbon atoms,
   (b) 3 to 8% by weight of at least one trialkanolamine,
   (c) 1 to 8% by weight of at least one nonionic emulsifier,
   (d) 0 to 3% by weight of a fatty alcohol or fatty alcohol mixture,
   (e) 0.1 to 6% by weight of one or more emollients,
   (f) 1 to 10% by weight propellant with a vapor pressure of 76 to 420 kPa at 20° C.,
   (g) 0.1 to 1% by weight of at least one cellulose derivative, and
   (h) 0.1 to 4% by weight of at lest one glycerol polyglycol ether isostearate,
   each in relation to the total weight of the preparation respectively,
   wherein the oil-in-water emulsion is free from fatty acid diethanolamides, and
   wherein the preparation is suitable for filling in an aerosol container.

2. The preparation as claimed in claim 1, wherein the at least one nonionic emulsifier is present in a concentration of 2 to 6% by weight.

3. The preparation as claimed in claim 1, wherein the at least one nonionic emulsifier includes a nonionic emulsifier with an HLB value of at least 14.

4. The preparation as claimed in claim 1, wherein the at least one nonionic emulsifier includes at least one nonionic emulsifier selected from the group consisting of fatty acid alkoxylates with 10 to 40 alkoxy units.

5. The preparation as claimed in claim 1, wherein the at least one nonionic emulsifier includes at least one nonionic emulsifier selected from the group consisting of fatty acid alkoxylates with 15 to 30 alkoxy units.

6. The preparation as claimed in claim 1, wherein the one or more emollients is present in a concentration of 0.5 to 5% by weight.

7. The preparation as claimed in claim 1, wherein the propellant is present in a concentration of 2 to 5% by weight.

8. The preparation as claimed in claim 1, wherein the at least one cellulose derivative includes at least one cellulose derivative selected from the group consisting of hydroxypropyl methylcellulose, hydroxyethylcellulose, and hydroxypropylcellulose.

9. The preparation as claimed in claim 1, wherein the at least one glycerol polyglycol ether isostearate is present in a concentration of 0.1 to 3% by weight.

10. The preparation as claimed in claim 1, wherein the at least one glycerol polyglycol ether isostearate is present in a concentration of 0.1 to.2% by weight.

11. The preparation as claimed in claim 1, wherein the at least one glycerol polyglycol ether isostearate includes at least one glycerol polyglycol ether isostearate with 70 to 110 ethylene oxide units.

12. The preparation as claimed in claim 1, wherein the at least one glycerol polyglycol ether isostearate includes glycerol polyglycol ether-90-isostearate.

13. The preparation as claimed in claim 1, wherein the preparation is a foam when extracted from a pressurized gas container.

14. The preparation as claimed in claim 13, wherein the oil content of the foam is 0 to 6% by weight.

15. The preparation as claimed in claim 1, wherein the preparation is a shaving gel extractable from a pressurized gas container.

16. The preparation as claimed in claim 15, wherein the oil content of the shaving gel is 0 to 2% by weight.

17. A pressurized gas container containing a preparation comprising an oil-in-water emulsion containing soap, the emulsion comprising:
   (a) 4 to 12% by weight of at least one fatty acid with 12 to 18 carbon atoms,
   (b) 3 to 8% by weight of at least one trialkanolamine,
   (c) 1 to 8% by weight of at least one nonionic emulsifier,
   (d) 0 to 3% by weight of a fatty alcohol or fatty alcohol mixture,
   (e) 0.1 to 6% by weight of one or more emollients,
   (f) 1 to 10% by weight propellant with a vapor pressure of 76 to 420 kPa at 20° C.,
   (g) 0.1 to 1% by weight of at least one cellulose derivative, and
   (h) 0.1 to 4% by weight of at lest one glycerol polyglycol ether isostearate,
   each in relation to the total weight of the preparation respectively,
   wherein the oil-in-water emulsion is free from fatty acid diethanolamides.

18. The pressurized gas container as claimed in claim 17, wherein the gas container includes two chambers.

* * * * *